United States Patent [19]

Zaiger et al.

[11] Patent Number: Plant 5,307

[45] Date of Patent: Oct. 30, 1984

[54] PLUM TREE (35-EA-220)

[76] Inventors: Chris F. Zaiger, 1907 Elm Ave.; Gary N. Zaiger, 537 Rosemore Ave.; Leith M. Gardner, 1207 Grimes Ave.; Grant G. Zaiger, 2121 Elm Ave., all of Modesto, Calif. 95351

[21] Appl. No.: 472,982

[22] Filed: Mar. 7, 1983

[51] Int. Cl.[3] ..... A01H 5/03

[52] U.S. Cl. ..... Plt./38

[58] Field of Search ..... Plt./38

*Primary Examiner*—Robert E. Bagwill

*Attorney, Agent, or Firm*—Roger B. Webster

[57] ABSTRACT

A new and distinct variety of plum tree which is of large size, vigorous, and semi-dense; foliated with medium size, mostly elliptical, some oblanceolate, leaves having a serrate margin, and globose glands; flowers from plump, free buds of medium size and length; the flowers being white; and is a regular and productive bearer of late maturing, large size, semi-freestone, globose fruit slightly flattened at the stem end, the fruit having bluish-red skin and firm, yellow flesh.

1 Drawing Figure

BACKGROUND OF THE VARIETY

1. Field of the Invention

In the field of plant genetics we conduct an extensive and continuing plant breeding program including the origination and asexual reproduction of orchard trees, and of which peaches, apricots, and plums are exemplary. It was against this background of our activities that the present variety of plum tree was originated and asexually reproduced by us in an experimental orchard located at Modesto, Stanislaus County, Calif.

2. Classification of the Variety

The present new and distinct variety of plum tree is embraced by Class 38, Plants, of the U.S. Patent Office Manual of Classification.

3. Prior Varieties

Among the existent varieties of plum trees which are known to us, and mentioned herein, are Santa Rosa (unpatented) and Roysum U.S. Plant Pat. No. 2,619).

ORIGIN OF THE VARIETY

The present variety of plum tree was originated by us, in the aforesaid experimental orchard, in the following manner:

Buds—from a Roysum bud stick previously irradiated with Cobalt 60—were budded into compatible rootstock, and—from the resulting trees—a selection was made. From this selection, open-pollinated seeds were collected and seedlings grown therefrom; such seedlings having been maintained under careful and continuing observation. In maturity, one of such seedlings, and which is the present variety, evidenced certain novel and distinctive characteristics and hence was selected for asexual reproduction in contemplation of potential commercialization.

ASEXUAL REPRODUCTION OF THE VARIETY

The present variety of plum tree was asexually reproduced, in the aforesaid experimental orchard, by grafting and budding, and such reproductions ran true to the original tree and its fruit in all respects.

SUMMARY OF THE VARIETY

The present variety of plum tree is, characteristically, of large size, vigorous, and semi-dense; foliated with medium size, mostly elliptical, some oblanceolate leaves having a serrate margin, and globose glands; flowers from plump, free buds of medium size and length; the flowers being white; and is a regular and productive bearer of late maturing, large size, semi-freestone, globose fruit slightly flattened at the stem end, the fruit having bluish-red skin and firm, yellow flesh.

The present variety of plum tree is further, and more particularly, characterized by blooming approximately two days later than the Santa Rosa, and by late ripening fruit; i.e., late in August but approximately ten days before the Roysum.

The present variety of plum tree is still further characterized by fruit, after picking at shipping ripe, which will hold in marketable condition in cold storage (34° to 38° F.) for three weeks; the fruit being of good fresh-fruit eating quality, and of very good keeping and long distance shipping quality.

The present variety of plum tree is still further characterized—in comparison to the Roysum—by fruit which evidences fewer and smaller skin cracks along the suture near the stem cavity.

BRIEF DESCRIPTION OF THE DRAWING

The drawing comprises illustrations, by photographic reproduction in color, of typical specimens of the foliage and firm-ripe fruit of the present variety of plum tree; such illustrations being of a twig with leaves, and separate fruit; one of the latter being cut in half to expose the flesh, with the stone remaining in one of the halves.

DESCRIPTION OF THE VARIETY

The botanical details of this new and distinct variety of plum tree—with color definitions (except those in common color terms) referenced to Reinhold Color Atlas by A. Kornerup and J. H. Wanscher—are as follows:

TREE

Size: Large.
Vigor: Vigorous.
Density: Semi-dense.
Production: Productive.
Bearing: Regular.

TRUNK

Size: Stocky.
Texture: Shaggy.

BRANCHES

Size: Medium.
Texture: Medium rough.

LEAVES

Size: Medium.
*Average length.*—4¼".
*Average width.*—1⅜".
Texture: Smooth.
Margin: Serrate.
Shape: Mostly elliptical. Some oblanceolate.
Glands:
*Number.*—Variable — 1 to 3, usually 2.
*form.*—Globose.
Petiole:
*Average length.*—⅝".
*Average width.*—1/16".
Color:
*Upper surface.*—Deep green (27-E-7 to 27-F-8).
*Lower surface.*—Grayish green (28-E-6 to 28-E-7).

FLOWER BUDS

Size: Medium.
Length: Medium.
Form: Plump. Free.

FLOWERS

Blooming period:
*Date of first bloom.*—Mar. 1, 1980.
*Date of full bloom.*—Mar. 4, 1980. Blooms approximately 2 days later than the Santa Rosa.
Color: White.

FRUIT

Maturity when described: Firm ripe.
Date of first picking: Aug. 20, 1980.
Date of last picking: Aug. 27, 1980.
Size: Large.
*Normal range.*—Axial diameter — 2¼" to 2-5/16".
*Normal range.* — Transverse in suture plane -2⅛" to 2¼".
Form: Variable. Usually symmetrical. Globose to slightly flattened at stem end.
Suture: Very shallow. Nearly smooth. Extends from base to apex.
Base: Retuse.
Apex: Rounded to slightly depressed.
Cavity: Rounded to slightly elongated in suture plane.
*Average depth.*—¼".
*Average breadth.*—7/16".
Stem:
*Average length.*—½".
*Average width.*—3/32".

SKIN

Thickness: Medium.
Texture: Medium.
Tendency to crack: Very slight. Very small percentage of fruit has small crack along suture near stem cavity.
Down: Wanting.
Bloom: Moderate to heavy.
Color: Bluish red (12-A-7 to 12-B-7) Suture slightly darker.

FLESH

Texture: Firm. Meaty.
Ripens: Evenly.
Flavor: Mild. Sub-acid.
Fibers: Few. Tender.
Eating quality: Good.
Color: Chrome yellow (5-A-8 to 5-B-7).

STONE

Type: Semi-freestone. Adheres slightly to flesh along suture.
Size:
*Average.*—¾".
*Average width.*—¾".
*Average thickness.*—5/16".
Surface: Irregularly furrowed. Ridged near base.
Sides: Equal.
Base: Straight.
Apex: Acuminate.
Color: Light brown (6-D-8 to 6-D-6).
Tendency to split: None.

USE

Market. Local and long distance shipping.

KEEPING QUALITY

Very good.

SHIPPING QUALITY

Very good.

The plum tree and its fruit herein described may vary in slight detail due to climatic and soil conditions under which the variety may be grown; the present description being of the variety as grown in the Central Valley of California.

We claim:

1. A new and distinct variety of plum tree, substantially as illustrated and described, characterized by late ripening, large size, semi-freestone, globose fruit slightly flattened at the stem end, the fruit having bluish-red skin and firm, yellow flesh; and further characterized by fruit which holds well in cold storage, is of good eating quality and very good keeping and long distance shipping quality, and—in comparison to the Roysum—ripens approximately ten days earlier and with fewer and smaller skin cracks along the suture near the stem cavity.

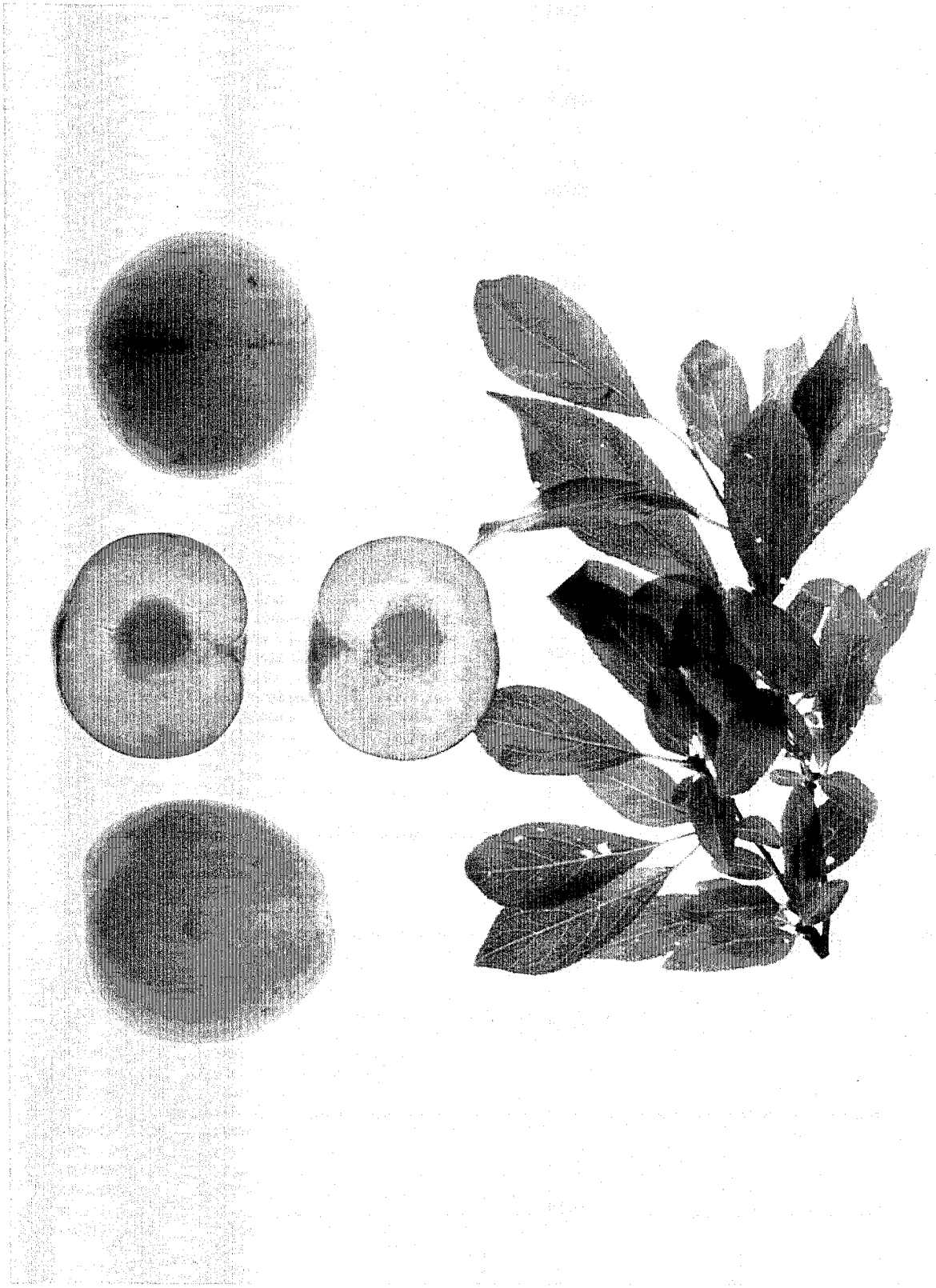

* * * * *